US009842121B2

(12) United States Patent
Konuma

(10) Patent No.: US 9,842,121 B2
(45) Date of Patent: Dec. 12, 2017

(54) MEDICAL INFORMATION PROCESSING APPARATUS TO APPLY IMAGE PROCESSING TO RECEIVED MEDICAL IMAGES

(71) Applicant: TOSHIBA MEDICAL SYSTEMS CORPORATION, Otawara-Shi (JP)

(72) Inventor: Nobuyuki Konuma, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 211 days.

(21) Appl. No.: 14/453,996

(22) Filed: Aug. 7, 2014

(65) Prior Publication Data
US 2015/0049933 A1 Feb. 19, 2015

(30) Foreign Application Priority Data
Aug. 19, 2013 (JP) ................................. 2013-169957

(51) Int. Cl.
G06K 9/00 (2006.01)
G06F 17/30 (2006.01)
G06F 19/00 (2011.01)

(52) U.S. Cl.
CPC ...... G06F 17/30244 (2013.01); G06F 19/321 (2013.01); G06F 19/327 (2013.01)

(58) Field of Classification Search
None
See application file for complete search history.

(56) References Cited

U.S. PATENT DOCUMENTS

| 6,298,112 | B1 * | 10/2001 | Acharya | A61B 6/032 378/15 |
| 2006/0083442 | A1 * | 4/2006 | Loukipoudis | G06F 19/321 382/305 |
| 2010/0049740 | A1 * | 2/2010 | Iwase | G06F 19/321 705/7.27 |
| 2013/0055222 | A1 * | 2/2013 | Darrow | G06F 8/54 717/140 |
| 2013/0208966 | A1 * | 8/2013 | Zhao | G06F 9/5072 382/131 |

FOREIGN PATENT DOCUMENTS

| JP | 2005-196253 | 7/2005 |
| JP | 2010-22727 | 2/2010 |

* cited by examiner

Primary Examiner — Nirav G Patel
(74) Attorney, Agent, or Firm — Oblon, McClelland, Maier & Neustadt, L.L.P.

(57) ABSTRACT

A medical information processing apparatus includes an exam reservation information receiver and an image processor. The exam reservation information receiver receives exam reservation information for multiple image generating apparatuses, from an exam reservation apparatus. The image processor determines a type of image processing based on the received exam reservation information, and applies the determined type of image processing to original images as medical images generated by the multiple image generating apparatuses to generate a processing result image as the medical image.

14 Claims, 20 Drawing Sheets

EXAM RESERVATION INFORMATION

| PATIENT IDENTIFYING INFORMATION | EXAM DETAILED INFORMATION | | | IMAGING TARGET SITE |
|---|---|---|---|---|
| | IMAGE GENERATING APPARATUS | IMAGING CONDITION (IMAGING METHOD) | | |
| PATIENT A | CT | NORMAL IMAGING + CONTRAST IMAGING | | HEART |
| | PET | --- | | |
| PATIENT B | CT | NORMAL IMAGING + CONTRAST IMAGING | | BRAIN |
| | MR | DTI | | |
| PATIENT C | CT | NORMAL IMAGING | | LIVER |
| | UL | --- | | |
| PATIENT D | CT | NORMAL IMAGING + CONTRAST IMAGING | | LARGE INTESTINE |
| | | --- | | |
| PATIENT E | CT | NORMAL IMAGING | | HEART |
| | PET | --- | | |

FIG. 3

EXAM EXECUTION INFORMATION

| PATIENT IDENTIFYING INFORMATION | | EXAM DETAILED INFORMATION | | | EXECUTION SITUATION INFORMATION |
|---|---|---|---|---|---|
| | | IMAGE GENERATING APPARATUS | IMAGING CONDITION (IMAGING METHOD) | IMAGING TARGET SITE | |
| EXAM A | SERIES 1 | CT | NORMAL IMAGING | HEART | COMPLETED |
| EXAM A | SERIES 2 | CT | CONTRAST IMAGING | | COMPLETED |
| EXAM A | SERIES 3 | PET | — | | IN PROGRESS |
| EXAM B | SERIES 1 | CT | NORMAL IMAGING | BRAIN | COMPLETED |
| EXAM B | SERIES 2 | CT | CONTRAST IMAGING | | IN PROGRESS |
| EXAM B | SERIES 3 | MR | DTI | | NOT EXECUTED |

FIG. 5

IMAGE PROCESSING CORRESPONDENCE TABLE

| IMAGE GENERATING APPARATUS | EXAM DETAILED INFORMATION | | IMAGE PROCESSING INFORMATION | TRANSFER DESTINATION OF PROCESSING RESULT IMAGE |
|---|---|---|---|---|
| | IMAGING CONDITION (IMAGING METHOD) | IMAGING TARGET SITE | | |
| CT | NORMAL IMAGING + CONTRAST IMAGING | HEART | CT IMAGE (NOMAL): EXTRACTION OF HEART MUSCLE<br>CT IMAGE (CONTRAST): EXTRACTION OF CORONARY ARTERY | CT, DIAGNOSTIC READING SYSTEM |
| PET | | | PET IMAGE: GENERATION OF HEART METABOLIC IMAGE<br>CT IMAGE (NOMAL) + PET IMAGE: 3D FUSION | MR, DIAGNOSTIC READING SYSTEM |
| CT | NORMAL IMAGING + CONTRAST IMAGING | BRAIN | CT IMAGE (CONTRAST): EXTRACTION OF BRAIN BLOOD VESSEL | |
| MR | DTI | | MR IMAGE: GENERATION OF TRACTOGRAPHY IMAGE<br>PET IMAGE: GENERATION OF HEART METABOLIC IMAGE<br>CT IMAGE (NOMAL) + MR IMAGE: 3D FUSION | |
| CT | NORMAL IMAGING | LIVER | CT IMAGE (NOMAL): MPR | UL |
| UL | | | | |
| CT | NORMAL IMAGING + CONTRAST IMAGING | LARGE INTESTINE | CT IMAGE (NOMAL): EXTRACTION OF LARGE INTESTINE<br>CT IMAGE (CONTRAST): GENERATION OF VE (VIRTUAL ENDOSCOPY) IMAGE | CT |
| CT | NORMAL IMAGING | HEART | CT IMAGE (NOMAL): EXTRACTION OF HEART MUSCLE<br>CT IMAGE (CONTRAST): EXTRACTION OF CORONARY ARTERY | DIAGNOSTIC READING SYSTEM |
| PET | | | PET IMAGE: GENERATION OF HEART METABOLIC IMAGE<br>CT IMAGE (NOMAL) + PET IMAGE: 3D FUSION | |

FIG. 7

SITUATION CORRESPONDENCE TABLE AT FIRST POINT IN TIME

| EXAM IDENTIFYING INFORMATION | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|
| | IMAGE GENERATING APPARATUS | IMAGING CONDITION (IMAGING METHOD) | | | | | | |
| | CT | NORMAL IMAGING | NOT EXECUTED | NOT RECEIVED | | | | |
| | CT | CONTRAST IMAGING | NOT EXECUTED | NOT RECEIVED | | | | |
| | PET | — | NOT EXECUTED | NOT RECEIVED | | | | |
| | CT | NORMAL IMAGING | NOT EXECUTED | NOT RECEIVED | | | | |
| | CT | CONTRAST IMAGING | NOT EXECUTED | NOT RECEIVED | | | | |
| | MR | DTI | NOT EXECUTED | NOT RECEIVED | | | | |

FIG. 10

SITUATION CORRESPONDENCE TABLE AT SECOND POINT IN TIME

| EXAM IDENTIFYING INFORMATION | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|
| | IMAGE GENERATING APPARATUS | IMAGING CONDITION (IMAGING METHOD) | | | | | | |
| | CT | NORMAL IMAGING | NOT EXECUTED | NOT RECEIVED | CT IMAGE (NORMAL) : EXTRACTION OF HEART MUSCLE | NOT PROCESSED | | |
| | CT | CONTRAST IMAGING | NOT EXECUTED | NOT RECEIVED | CT IMAGE (CONTRAST) : EXTRACTION OF CORONARY ARTERY | NOT PROCESSED | CT | NOT TRANSMITTED |
| | PET | — | NOT EXECUTED | NOT RECEIVED | PET IMAGE : GENERATION OF HEART METABOLIC IMAGE | NOT PROCESSED | | |
| | | | | | CT IMAGE (NORMAL) + PET IMAGE : 3D FUSION | NOT PROCESSED | DIAGNOSTIC READING SYSTEM | NOT TRANSMITTED |
| | CT | NORMAL IMAGING | NOT EXECUTED | NOT RECEIVED | CT IMAGE (CONTRAST) : EXTRACTION OF BRAIN BLOOD VESSEL | NOT PROCESSED | | |
| | CT | CONTRAST IMAGING | NOT EXECUTED | NOT RECEIVED | MR IMAGE : GENERATION OF TRACTOGRAPHY IMAGE | NOT PROCESSED | MR | NOT TRANSMITTED |
| | MR | DTI | NOT EXECUTED | NOT RECEIVED | CT IMAGE (NORMAL) + MR IMAGE : 3D FUSION | NOT PROCESSED | DIAGNOSTIC READING SYSTEM | NOT TRANSMITTED |

FIG. 11

SITUATION CORRESPONDENCE TABLE AT THIRD POINT IN TIME

| EXAM IDENTIFYING INFORMATION | | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|---|
| | | IMAGE GENERATING APPARATUS | IMAGING CONDITION (IMAGING METHOD) | | | | | | |
| EXAM A | SERIES 1 | CT | NORMAL IMAGING | COMPLETED | NOT RECEIVED | CT IMAGE (NOMAL) : EXTRACTION OF HEART MUSCLE | NOT PROCESSED | | NOT TRANSMITTED |
| EXAM A | SERIES 2 | CT | CONTRAST IMAGING | COMPLETED | NOT RECEIVED | CT IMAGE (CONTRAST) : EXTRACTION OF CORONARY ARTERY | NOT PROCESSED | CT | |
| EXAM A | SERIES 3 | PET | — | IN PROGRESS | NOT RECEIVED | PET IMAGE : GENERATION OF HEART METABOLIC IMAGE | NOT PROCESSED | | |
| EXAM A | | | | | | CT IMAGE (NOMAL) + PET IMAGE : 3D FUSION | NOT PROCESSED | DIAGNOSTIC READING SYSTEM | NOT TRANSMITTED |
| EXAM B | SERIES 1 | CT | NORMAL IMAGING | IN PROGRESS | NOT RECEIVED | CT IMAGE (CONTRAST) : EXTRACTION OF BRAIN BLOOD VESSEL | NOT PROCESSED | MR | NOT TRANSMITTED |
| EXAM B | SERIES 2 | CT | CONTRAST IMAGING | NOT EXECUTED | NOT RECEIVED | MR IMAGE : GENERATION OF TRACTOGRAPHY IMAGE | NOT PROCESSED | | |
| EXAM B | SERIES 3 | MR | DTI | NOT EXECUTED | NOT RECEIVED | CT IMAGE (NOMAL) + MR IMAGE : 3D FUSION | NOT PROCESSED | DIAGNOSTIC READING SYSTEM | NOT TRANSMITTED |

FIG. 12

SITUATION CORRESPONDENCE TABLE AT FOURTH POINT IN TIME

| EXAM IDENTIFYING INFORMATION | | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|---|
| | | IMAGE GENERATING APPARATUS | IMAGING CONDITION (IMAGING METHOD) | | | | | | |
| EXAM A | SERIES 1 | CT | NORMAL IMAGING | COMPLETED | COMPLETED | CT IMAGE (NOMAL) : EXTRACTION OF HEART MUSCLE | NOT PROCESSED | CT | NOT TRANSMITTED |
| EXAM A | SERIES 2 | CT | CONTRAST IMAGING | COMPLETED | IN RECEPTION | CT IMAGE (CONTRAST) : EXTRACTION OF CORONARY ARTERY | NOT PROCESSED | | |
| EXAM A | SERIES 3 | PET | — | COMPLETED | IN RECEPTION | PET IMAGE : GENERATION OF HEART METABOLIC IMAGE | NOT PROCESSED | DIAGNOSTIC READING SYSTEM | NOT TRANSMITTED |
| | | | | | | CT IMAGE (NOMAL) + PET IMAGE : 3D FUSION | NOT PROCESSED | | |
| EXAM B | SERIES 1 | CT | NORMAL IMAGING | COMPLETED | NOT RECEIVED | CT IMAGE (CONTRAST) : EXTRACTION OF BRAIN BLOOD VESSEL | NOT PROCESSED | MR | NOT TRANSMITTED |
| EXAM B | SERIES 2 | CT | CONTRAST IMAGING | IN PROGRESS | NOT RECEIVED | MR IMAGE : GENERATION OF TRACTOGRAPHY IMAGE | NOT PROCESSED | DIAGNOSTIC READING SYSTEM | NOT TRANSMITTED |
| EXAM B | SERIES 3 | MR | DTI | NOT EXECUTED | NOT RECEIVED | CT IMAGE (NOMAL) + MR IMAGE : 3D FUSION | NOT PROCESSED | | |

FIG. 13

SITUATION CORRESPONDENCE TABLE AT FIFTH POINT IN TIME

| EXAM IDENTIFYING INFORMATION | | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|---|
| | | IMAGE GENERATING APPARATUS | IMAGING CONDITION (IMAGING METHOD) | | | | | | |
| EXAM A | SERIES 1 | CT | NORMAL IMAGING | COMPLETED | COMPLETED | CT IMAGE (NOMAL) : EXTRACTION OF HEART MUSCLE | COMPLETED | CT | NOT TRANSMITTED |
| EXAM A | SERIES 2 | CT | CONTRAST IMAGING | COMPLETED | COMPLETED | CT IMAGE (CONTRAST) : EXTRACTION OF CORONARY ARTERY | COMPLETED | | |
| EXAM A | SERIES 3 | PET | — | COMPLETED | COMPLETED | PET IMAGE : GENERATION OF HEART METABOLIC IMAGE | COMPLETED | DIAGNOSTIC READING SYSTEM | NOT TRANSMITTED |
| | | | | | | CT IMAGE (NOMAL) + PET IMAGE : 3D FUSION | COMPLETED | | |
| EXAM B | SERIES 1 | CT | NORMAL IMAGING | COMPLETED | COMPLETED | CT IMAGE (CONTRAST) : EXTRACTION OF BRAIN BLOOD VESSEL | IN PROCESS | MR | NOT TRANSMITTED |
| EXAM B | SERIES 2 | CT | CONTRAST IMAGING | COMPLETED | COMPLETED | MR IMAGE : GENERATION OF TRACTOGRAPHY IMAGE | NOT PROCESSED | DIAGNOSTIC READING SYSTEM | NOT TRANSMITTED |
| EXAM B | SERIES 3 | MR | DTI | NOT EXECUTED | NOT RECEIVED | CT IMAGE (NOMAL) + MR IMAGE : 3D FUSION | NOT PROCESSED | | |

FIG. 14

SITUATION CORRESPONDENCE TABLE AT SIXTH POINT IN TIME

| EXAM IDENTIFYING INFORMATION | | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|---|
| | | IMAGE GENERATING APPARATUS | IMAGING CONDITION (IMAGING METHOD) | | | | | | |
| EXAM A | SERIES 1 | CT | NORMAL IMAGING | COMPLETED | COMPLETED | CT IMAGE (NOMAL) : EXTRACTION OF HEART MUSCLE | COMPLETED | | |
| EXAM A | SERIES 2 | CT | CONTRAST IMAGING | COMPLETED | COMPLETED | CT IMAGE (CONTRAST) : EXTRACTION OF CORONARY ARTERY | COMPLETED | CT | COMPLETED |
| EXAM A | SERIES 3 | PET | — | COMPLETED | COMPLETED | PET IMAGE : GENERATION OF HEART METABOLIC IMAGE | COMPLETED | | |
| | | | | | | CT IMAGE (NOMAL) + PET IMAGE : 3D FUSION | COMPLETED | DIAGNOSTIC READING SYSTEM | IN TRANSMISSION |
| EXAM B | SERIES 1 | CT | NORMAL IMAGING | COMPLETED | COMPLETED | CT IMAGE (CONTRAST) : EXTRACTION OF BRAIN BLOOD VESSEL | COMPLETED | MR | NOT TRANSMITTED |
| EXAM B | SERIES 2 | CT | CONTRAST IMAGING | COMPLETED | COMPLETED | MR IMAGE : GENERATION OF TRACTOGRAPHY IMAGE | IN PROCESS | | |
| EXAM B | SERIES 3 | MR | DTI | IN PROGRESS | NOT RECEIVED | CT IMAGE (NOMAL) + MR IMAGE : 3D FUSION | NOT PROCESSED | DIAGNOSTIC READING SYSTEM | NOT TRANSMITTED |

SITUATION CORRESPONDENCE TABLE AT FIRST POINT IN TIME

| EXAM IDENTIFYING INFORMATION | | EXAM DETAILED INFORMATION | | EXECUTION SITUATION INFORMATION | RECEPTION SITUATION INFORMATION | IMAGE PROCESSING INFORMATION | | | |
|---|---|---|---|---|---|---|---|---|---|
| | | IMAGE GENERATING APPARATUS | IMAGING CONDITION (IMAGING METHOD) | | | | PROCESSING SITUATION INFORMATION | TRANSFER DESTINATION OF PROCESSING RESULT IMAGE | TRANSMISSION SITUATION INFORMATION |
| EXAM A | SERIES 1 | CT | NORMAL IMAGING | COMPLETED | COMPLETED | | | | |

SITUATION CORRESPONDENCE TABLE AT SECOND POINT IN TIME

| EXAM IDENTIFYING INFORMATION | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|
| | IMAGE GENERATING APPARATUS | IMAGING CONDITION (IMAGING METHOD) | | | | | | |
| EXAM A SERIES 1 | CT | NORMAL IMAGING | COMPLETED | COMPLETED | CT IMAGE (NOMAL) : EXTRACTION OF HEART MUSCLE | NOT PROCESSED | CT | NOT TRANSMITTED |
| EXAM A SERIES 2 | CT | CONTRAST IMAGING | COMPLETED | COMPLETED | CT IMAGE (CONTRAST) : EXTRACTION OF CORONARY ARTERY | NOT PROCESSED | | |
| EXAM A SERIES 3 | PET | --- | COMPLETED | COMPLETED | PET IMAGE : GENERATION OF HEART METABOLIC IMAGE | NOT PROCESSED | DIAGNOSTIC READING SYSTEM | NOT TRANSMITTED |
| | | | | | CT IMAGE (NOMAL) + PET IMAGE : 3D FUSION | NOT PROCESSED | | |

FIG. 17

SITUATION CORRESPONDENCE TABLE AT THIRD POINT IN TIME

| EXAM IDENTIFYING INFORMATION | | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|---|
| | | IMAGE GENERATING APPARATUS | IMAGING CONDITION (IMAGING METHOD) | | | | | | |
| EXAM A | SERIES 1 | CT | NORMAL IMAGING | COMPLETED | COMPLETED | CT IMAGE (NOMAL) : EXTRACTION OF HEART MUSCLE | COMPLETED | | |
| EXAM A | SERIES 2 | CT | CONTRAST IMAGING | COMPLETED | COMPLETED | CT IMAGE (CONTRAST) : EXTRACTION OF CORONARY ARTERY | COMPLETED | CT | NOT TRANSMITTED |
| EXAM A | SERIES 3 | PET | — | COMPLETED | COMPLETED | PET IMAGE : GENERATION OF HEART METABOLIC IMAGE | COMPLETED | | |
| EXAM A | | | | | | CT IMAGE (NOMAL) + PET IMAGE : 3D FUSION | COMPLETED | DIAGNOSTIC READING SYSTEM | NOT TRANSMITTED |
| EXAM B | SERIES 1 | CT | NORMAL IMAGING | COMPLETED | COMPLETED | | | | |
| EXAM B | SERIES 2 | CT | CONTRAST IMAGING | COMPLETED | COMPLETED | | | | |

FIG. 18

SITUATION CORRESPONDENCE TABLE AT FOURTH POINT IN TIME

| EXAM IDENTIFYING INFORMATION | | EXAM DETAILED INFORMATION | | EXECUTION SITUATION INFORMATION | RECEPTION SITUATION INFORMATION | IMAGE PROCESSING INFORMATION | PROCESSING SITUATION INFORMATION | TRANSFER DESTINATION OF PROCESSING RESULT IMAGE | TRANSMISSION SITUATION INFORMATION |
|---|---|---|---|---|---|---|---|---|---|
| | | IMAGE GENERATING APPARATUS | IMAGING CONDITION (IMAGING METHOD) | | | | | | |
| EXAM A | SERIES 1 | CT | NORMAL IMAGING | COMPLETED | COMPLETED | CT IMAGE (NOMAL) : EXTRACTION OF HEART MUSCLE | COMPLETED | | |
| EXAM A | SERIES 2 | CT | CONTRAST IMAGING | COMPLETED | COMPLETED | CT IMAGE (CONTRAST) : EXTRACTION OF CORONARY ARTERY | COMPLETED | CT | COMPLETED |
| EXAM A | SERIES 3 | PET | — | COMPLETED | COMPLETED | PET IMAGE : GENERATION OF HEART METABOLIC IMAGE | COMPLETED | | |
| | | | | | | CT IMAGE (NOMAL) + PET IMAGE : 3D FUSION | COMPLETED | DIAGNOSTIC READING SYSTEM | IN TRANSMISSION |
| EXAM B | SERIES 1 | CT | NORMAL IMAGING | COMPLETED | COMPLETED | CT IMAGE (CONTRAST) : EXTRACTION OF BRAIN BLOOD VESSEL | COMPLETED | MR | NOT TRANSMITTED |
| EXAM B | SERIES 2 | CT | CONTRAST IMAGING | COMPLETED | COMPLETED | MR IMAGE : GENERATION OF TRACTOGRAPHY IMAGE | IN PROCESS | | |
| EXAM B | SERIES 3 | MR | DTI | COMPLETED | COMPLETED | CT IMAGE (NOMAL) + MR IMAGE : 3D FUSION | NOT PROCESSED | DIAGNOSTIC READING SYSTEM | NOT TRANSMITTED |

FIG. 19

MEDICAL INFORMATION PROCESSING APPARATUS TO APPLY IMAGE PROCESSING TO RECEIVED MEDICAL IMAGES

CROSS-REFERENCE TO RELATED APPLICATION

This application is based upon and claims the benefit of priority from Japanese Patent Application No. 2013-169957, filed on Aug. 19, 2013, the entire contents of which are incorporated herein by reference.

FIELD

An embodiment as an aspect of a present invention relates to a medical information processing apparatus that processes medical information.

BACKGROUND

HISs (hospital information systems), originally for processing medical remuneration, have recently been developed and expanded to be utilized as service monitoring systems in many medical institutions. Online exam data, electronic medical charts, and the like have started to be developed for the sake of enhancing the systems to allow information of HIS to be used not only for service management but also for medical care for patients. Manufacturers of image generating apparatuses (modalities) have conformed to the DICOM (digital imaging and communications in medicine) standard, which is a standard format in the medical field, for exchanging information through connection with computers of other manufacturers in the same industry, thus acquiring patient identifying information and the like through connection with the image generating apparatuses (diagnostic imaging apparatuses).

More specifically, a HIS/RIS (radiology information system) installed in each hospital uses MWM (modality worklist management) in conformity with the DICOM standard, adds patient identifying information to DICOM tags, and acquires the entries.

There are medical image information systems that transmit original images (medical images before being subjected to image processing) collected by image generating apparatuses, such as an X-ray imaging apparatus, an ultrasonographic apparatus, an X-ray CT (computed tomography) apparatus, an MRI (magnetic resonance imaging) apparatus and a PET (positron emission tomography) apparatus, and information related to these images, such as patient identifying information, via a DICOM network to image management apparatuses and MPPS (modality performed procedure step) servers, to thus collect information, and then extract the original images and related information as necessary and are operated for diagnosing patients using the images and information.

Recent advancement in medical science and imaging apparatuses from the conventional art diversifies image generating apparatuses used for exams. There are increasing cases of collecting multiple types of original images through multiple types of image generating apparatuses even for one disease. Furthermore, there are increasing cases of creating a fused image as a processing result image (medical image having been subjected to image processing) based on multiple types of original images such that the advantages of each of original images (properties: morphological images/functional images) are sufficiently taken from the multiple types of original images and of using the fused image for diagnosis and treatment.

Unfortunately, according to the conventional art, creation of a fused image based on multiple types of original images requires data collected through different image generating apparatuses. Accordingly, in many cases, acquisition of the original images from locations where these images are stored still requires time and effort.

Conventionally, in the case of creating a fused image using two or more types of original images collected through multiple image generating apparatuses, the two or more types of original images are collected into an image processing apparatus for creating a fused image. After the two or more types of original images become available in the image processing apparatus, an operator selects original images to be used for creating a fused image from among these two or more types, and causes an application to diagnostic read the images, thereby generating a fused image from the two or more types of original images. This case requires time for (transferring the two or more types of original images)+(selecting original images)+(fusion process). This case thus requires time and effort (waiting time) until starting to diagnostic read a fused image.

It is not uncommon for recent image generating apparatuses to create a group of several thousand original images at one time of exam (imaging). It unfortunately takes several tens of seconds to several minutes to transfer the group of original images to another apparatus. For instance, the transfer rate of original images is approximately 20 to 50 [images/second].

In a process of generating a 3D fused image based on a CT image and an MR image as original images, waiting time for image processing ranges from several minutes to several tens of minutes for generating an MR tractography image without consideration of imaging time; note that the variation in time depends also on the gap of a slice thickness or the like.

In a process of generating a 3D fused image based on a CT image and a PET image as original images, waiting time after selection of a group of original images ranges from several tens of seconds to several minutes or a little longer for executing an extraction process, a positioning process and a fusion process. Furthermore, achievement of highly accurate positioning sometimes requires a time period several times longer than the foregoing time period.

BRIEF DESCRIPTION OF THE DRAWINGS

In accompanying drawings,

FIG. 3 is a diagram showing an example of the exam reservation information;

FIG. 5 is a diagram showing an example of exam execution information;

FIG. 7 is a diagram showing an example of an image processing correspondence table;

FIG. 10 is a diagram showing an example of the situation correspondence table at a first point in time;

FIG. 11 is a diagram showing an example of the situation correspondence table at a second point in time;

FIG. 12 is a diagram showing an example of the situation correspondence table at a third point in time;

FIG. 13 is a diagram showing an example of the situation correspondence table at a fourth point in time;

FIG. 14 is a diagram showing an example of the situation correspondence table at a fifth point in time;

FIG. 15 is a diagram showing an example of the situation correspondence table at a sixth point in time;

FIG. 16 is a diagram showing an example of the situation correspondence table at a first point in time;

FIG. 17 is a diagram showing an example of the situation correspondence table at a second point in time;

FIG. 18 is a diagram showing an example of the situation correspondence table at a third point in time; and FIG. 19 is a diagram showing an example of the situation correspondence table at a fourth point in time.

DETAILED DESCRIPTION

A medical information processing apparatus according to a present embodiment is described with reference to the accompanying drawings.

To solve the above-described problems, the present embodiment provide the medical information processing apparatus, including: an exam reservation information receiver configured to receive exam reservation information for multiple image generating apparatuses, from an exam reservation apparatus; and an image processor configured to determine a type of image processing based on the received exam reservation information, and to apply the determined type of image processing to original images as medical images generated by the multiple image generating apparatuses to generate a processing result image as the medical image.

To solve the above-described problems, the present embodiment provide the medical information processing apparatus, including: an exam execution information receiver configured to receive exam execution information from multiple image generating apparatuses, the exam execution information representing an exam execution situation; and an image processor configured to determine a type of image processing based on the received exam execution information, and to apply the determined type of image processing to original images as medical images generated by the multiple image generating apparatuses to generate a processing result image as the medical image.

Figure 1:
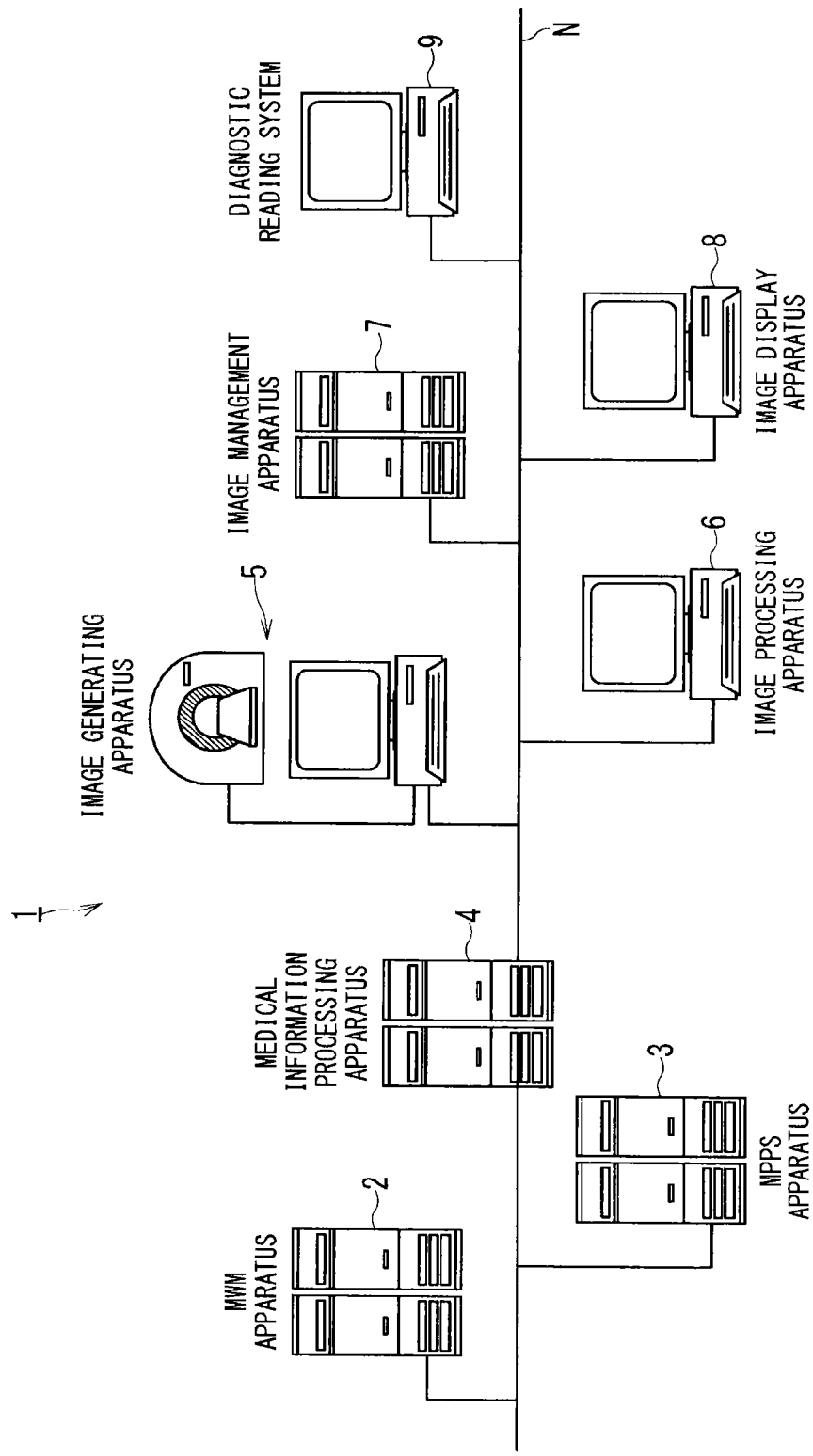
FIG. 1 is a schematic diagram showing a configuration of a medical information processing system.

FIG. 1 is a schematic diagram showing a configuration of a medical information processing system.

FIG. 1 shows a medical information processing system 1. The medical information processing system 1 includes an MWM apparatus (MWM server) 2, an MPPS apparatus (MPPS server) 3, a medical information processing apparatus (monitoring server) 4 according to a present embodiment, an image generating apparatus (modality) 5, an image processing apparatus (work station) 6, an image management apparatus (image server) 7, an image display apparatus 8, and a diagnostic reading system 9.

In the medical information processing system 1 shown in FIG. 1, the medical information processing apparatus 4 is provided separately from the image management apparatus 7 and the diagnostic reading system 9. However, the configuration is not limited to this case. Alternatively, a function of an after-mentioned medical information processing apparatus 4 may be provided in the image management apparatus 7 or the diagnostic reading system 9.

The MWM apparatus 2, the MPPS apparatus 3, the medical information processing apparatus 4, the image generating apparatus 5, the image processing apparatus 6, the image management apparatus 7, the image display apparatus 8, and the diagnostic reading system 9 have computer-based configurations. The MWM apparatus 2, the MPPS apparatus 3, the medical information processing apparatus 4, the image generating apparatus 5, the image processing apparatus 6, the image management apparatus 7, the image display apparatus 8, and the diagnostic reading system 9 are connected to each other via a hospital main DICOM network N in a mutually communicable manner.

Figure 2:
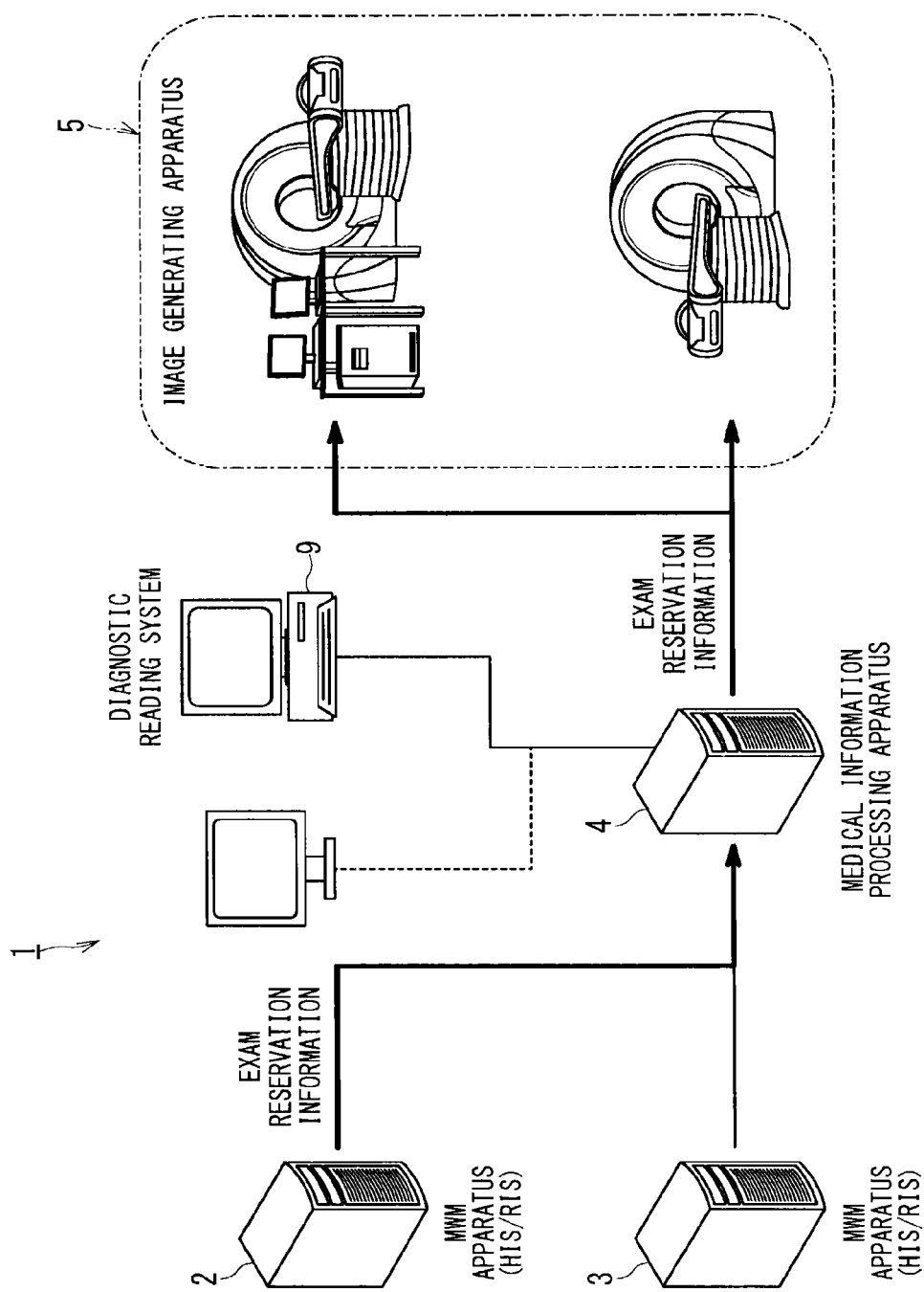
FIG. 2 is a diagram showing a flow of exam reservation information received by an MWM apparatus.

The MWM apparatus 2 receives exam reservation information (information on an exam reservation list) of the HIS/RIS, and transmits the exam reservation information as DICOM_MWM to the medical information processing apparatus 4. Patient identifying information is information for identifying a patient, such as a patient ID (identification). Exam detailed information is information for identifying an exam. FIG. 2 is a diagram showing a flow of the exam reservation information received by the MWM apparatus 2.

FIG. 3 is a diagram showing an example of the exam reservation information.

FIG. 3 shows pieces of the exam reservation information on five patients (patients A to E). As shown in FIG. 3, the exam reservation information contains the patient identifying information and the exam detailed information, which are associated with each other. The patient identifying information contains patient IDs (patient A, patient B, . . . ). The exam detailed information contains at least one of the type(s) of the image generating apparatus(es) 5, the imaging condition(s) (imaging method(s)) in the image generating apparatus(es) 5 and an imaging target site. Hereinafter, a case is described where the exam detailed information contains all the types of the image generating apparatus(es) 5, and the imaging conditions and the imaging target site(s) in the image generating apparatus(es) 5.

For instance, the top entry shows the exam reservation information that is on the patient A, pertains to a cardiac exam and represents that an X-ray CT apparatus as an image generating apparatus 5 performs normal imaging (non-contrast imaging) and contrast imaging and a PET apparatus as another image generating apparatus 5 performs imaging.

Figure 4:
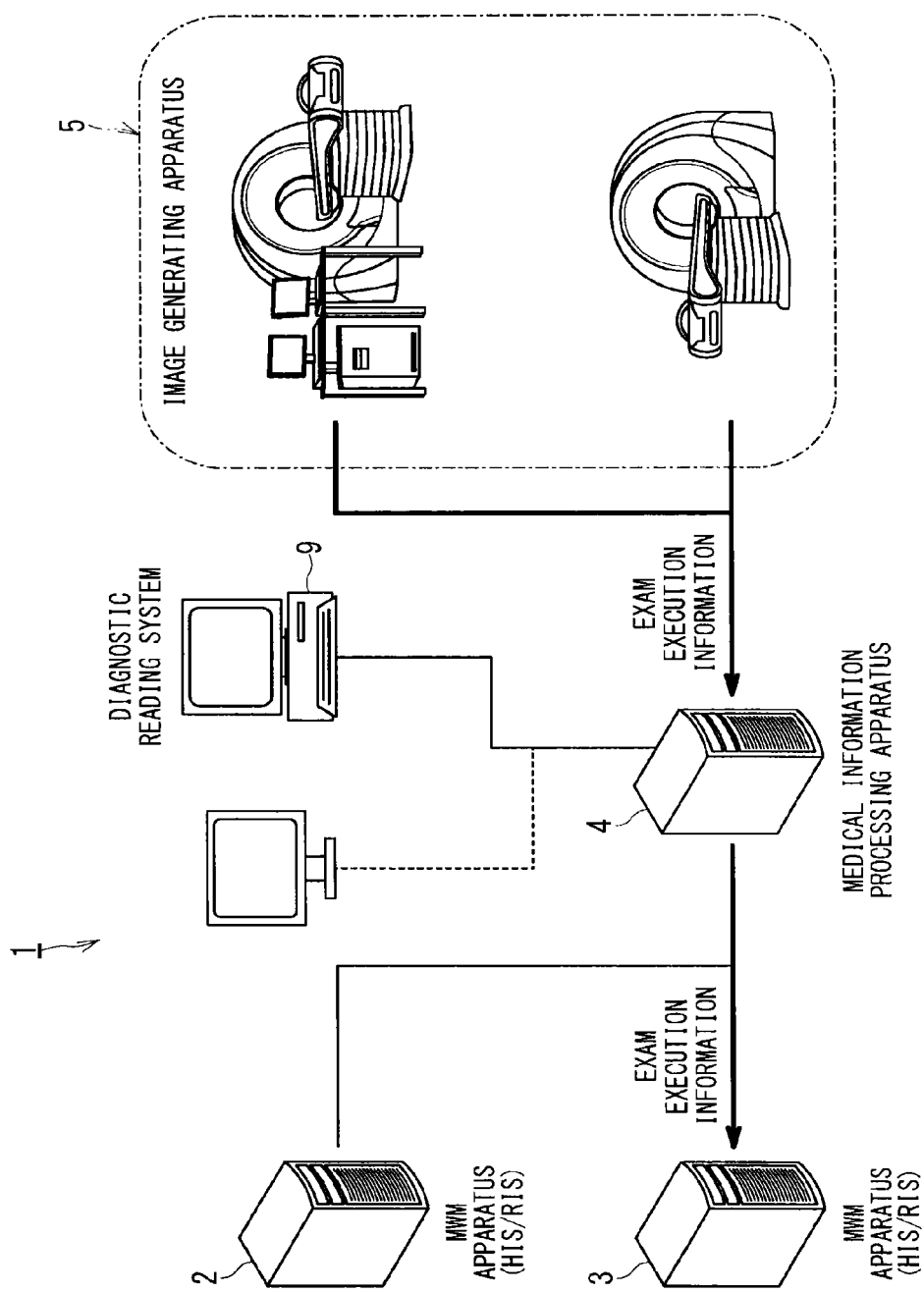
FIG. 4 is a diagram showing a flow of the exam execution information generated by an image generating apparatus.

Referring back to FIG. 1, the MPPS apparatus 3 receives, as DICOM_MPPS, exam execution information that represents an exam execution situation generated by the image generating apparatus 5 before or after execution of the exam, via the medical information processing apparatus 4. FIG. 4 is a diagram showing a flow of the exam execution information generated by the image generating apparatus 5.

Referring back to FIG. 1, the medical information processing apparatus 4 receives the exam reservation information as DICOM_MWM, from the MWM apparatus 2, and then transmits the information to the image generating apparatus 5 (shown in FIG. 2). The medical information processing apparatus 4 receives the exam execution information as DICOM_MPPS from the image generating apparatus 5, and then transmits the information to the MPPS apparatus 7 (shown in FIG. 4). The medical information processing apparatus 4 processes (monitors) the exam execution situation in the image generating apparatus 5, on the basis of the exam reservation information received from the MWM apparatus 2 and the exam execution information received from the image generating apparatus 5.

The image generating apparatus 5 receives the exam reservation information from the medical information processing apparatus 4, executes the exam according to the exam reservation information to generate an original image (a medical image having not been subjected to image processing), generates the exam execution information before or after execution of the exam, and transmits the exam execution information to the medical information processing apparatus 4.

FIG. 5 is a diagram showing an example of the exam execution information.

FIG. 5 shows the exam execution information that contains exam identifying information, exam identifying information detailed information, and execution situation information. As shown in FIG. 5, the exam execution information (execution situation information) is generated for each piece of exam identifying information (for each series). For instance, execution situation information that is on a series 1 of an exam A and becomes "completed", which represents that normal cardiac imaging (non-contrast imaging) through the X-ray CT apparatus as the image generating apparatus 5 has been completed.

Referring back to FIG. 1, the image generating apparatus 5 may be an X-ray diagnostic imaging apparatus, an ultrasonic apparatus, an X-ray CT (computed tomography) apparatus, an MRI (magnetic resonance imaging) apparatus, a nuclear medical diagnostic apparatus or the like. Typically, multiple image generating apparatuses 5 are connected to the DICOM network N. The image generating apparatus 5 generates an original image on an object, such as an imaging target site of a patient, in association with supplementary information.

The image processing apparatus 6 applies image processing to the original images generated by the image generating apparatus 5.

The image management apparatus 7 acquires processing result images (intermediate images: medical images having been subjected to image processing) taken by the medical information processing apparatus 4 and the image processing apparatus 6, and stores the images. The image management apparatus 7 is a DB (data base) server. The image management apparatus 7 is a medical image management system (PACS: picture archiving and communication system). The PACS can accept a request issued from the image display apparatus (a client, such as a viewer) 8, retrieve image data pursuant to the request, and transfer the data to the image display apparatus 8. The PACS can store, view and manage the original images received from the image generating apparatus 5, and integrally manage the original images through DICOM.

The image display apparatus 8 requests image data from the image management apparatus 7, and displays the image data transferred as a result of the request.

The diagnostic reading system 9 displays images, such as processing result images, generated by the medical information processing apparatus 4 and image processing apparatus 6, and generates a diagnostic reading report according to an operation by a diagnostic reader.

Figure 6:
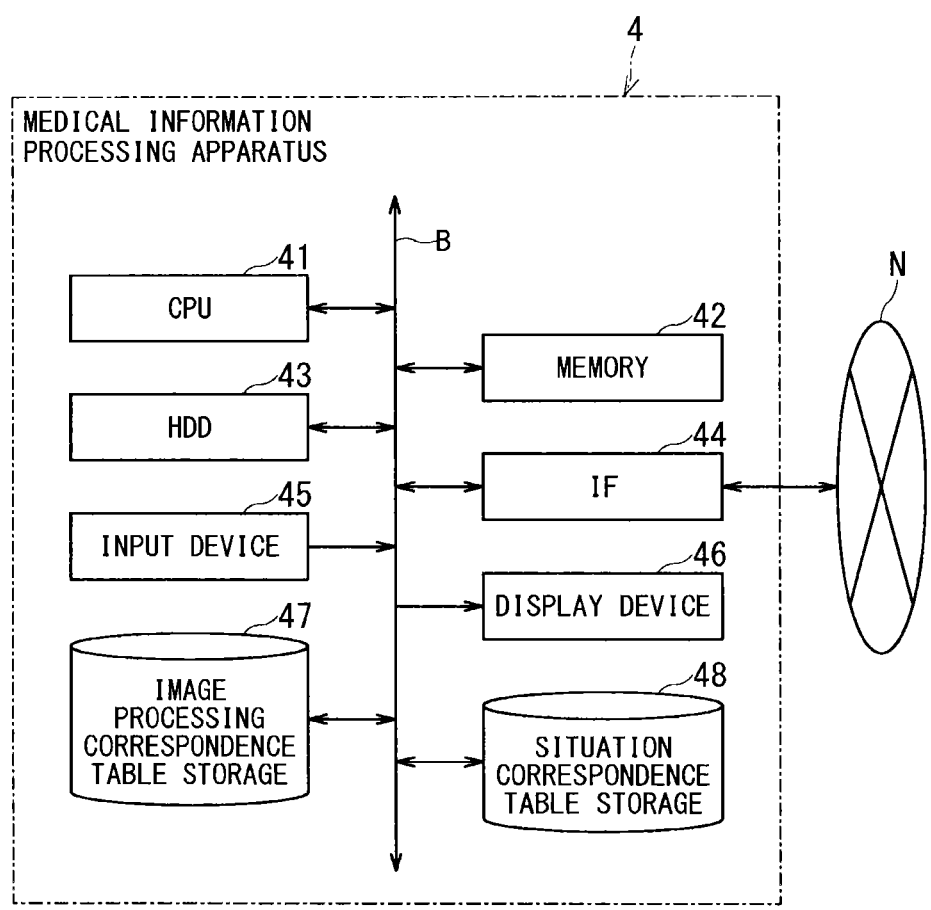
FIG. 6 is a diagram showing an example of a hardware configuration of a medical information processing apparatus according to a present embodiment.

FIG. 6 is a diagram showing an example of hardware configuration of the medical information processing apparatus 4 according to the present embodiment.

FIG. 6 shows the hardware configuration of the medical information processing apparatus 4. The medical information processing apparatus 4 mainly includes: basic pieces of hardware, such as a CPU (central processing unit) 41 as a control device, a memory 42, a HDD (hard disc drive) 43, an IF (interface) 44, an input device 45 and a display device 46; and an image processing correspondence table storage 47 and a situation correspondence table storage 48. The CPU 41 is mutually connected to each of hardware configuration elements configuring the medical information processing apparatus 4, via a bus B as a common signal transmission path.

The CPU 41 is a control device having a configuration of a large scale integrated circuit (LSI) including electronic circuits made of semiconductors enclosed in a package having multiple terminals. The CPU 41 executes a program stored in the memory 42. Furthermore, the CPU 41 has a function of loading programs stored in the HDD 43 and programs and the like transferred from the DICOM network N, received by the IF 44 and installed in the HDD 43 into the memory 42, and of executing the programs.

The memory 42 is a storing device including a ROM (read only memory) and a RAM (random access memory). The memory 42 has functions of storing IPL (initial program loading), BIOS (basic input/output system) and data, serving as a working memory of the CPU 41, and being used for temporarily storing data.

The HDD 43 is a storing device that has a configuration of enclosing metal disks onto which magnetic material is applied or evaporated in a reading device (not shown) in an undetachable manner. The HDD 43 has a function of storing programs installed in the medical information processing apparatus 4 (including not only application programs but also an OS (operating system) and the like) and various types of data.

The IF 44 includes connectors in conformity with parallel connecting specifications and serial connecting specifications. The IF 44 has functions capable of controlling communications in conformity with each standard for connection with the DICOM network N. These functions connect the medical information processing apparatus 4 to the DICOM network N.

The input device 45 may be a keyboard, a mouse and the like through which an operator can perform operations. Input signals according to the operation through the input device 45 are transmitted to the CPU 41 via the bus B.

The display device 46 includes a D/A (digital to analog) converter circuit and a monitor, which are not shown.

The image processing correspondence table storage 47 includes an HDD and a memory, and stores an image processing correspondence table that indicates correspondence relationship between the exam detailed information contained in the exam reservation information (shown in FIG. 3) and image processing information (type of image processing). The image processing correspondence table storage 47 preliminarily contains the image processing information for acquiring a processing result image having a high possibility of being used by the operator (diagnostic reader).

FIG. 7 is a diagram showing, an example of the image processing correspondence table.

As shown in FIG. 7, the image processing correspondence table contains the exam detailed information and the image processing information, which are associated with each other. The exam detailed information contains the type(s) of image generating apparatus(es) 5, the imaging condition(s) (imaging method(s)) in the image generating apparatus(es)

5, and imaging target site(s). One or more pieces of image processing information are assigned to each piece of exam detailed information.

For instance, the top entry shows a case of exam detailed information that is on a cardiac exam and represents that the X-ray CT apparatus as an image generating apparatus 5 performs normal imaging (non-contrast imaging) and contrast imaging and the PET apparatus as another image generating apparatus 5 performs imaging. In this case, the image processing is assigned a myocardium extracting process from original images based on normal imaging by the X-ray CT apparatus, a coronary artery extracting process from original images based on contrast imaging by the X-ray CT apparatus, a process of generating cardiac metabolism images that acquires a cardiac metabolism image as a processing result image from original images based on imaging by the PET apparatus, and a 3D fusion process from original images based on normal imaging by the X-ray CT apparatus and original images based on imaging by the PET apparatus. Alternatively, the exam detailed information may be assigned a transfer destination of the processing result image.

Referring back to FIG. 6, the situation correspondence table storage 48 includes a HDD or a memory, and stores the situation correspondence table (shown in FIGS. 10 to 15) represents correspondence relationship between the exam reservation information, the image processing information, the situation information (execution situation information, reception situation information, processing situation information, and transmission situation information), and the transfer destination of a processing result image. In the situation correspondence table in the situation correspondence table storage 48, the exam reservation information, the image processing information, the situation information, and the transfer destination of the processing result image are appropriately registered and updated. Methods of registering and updating the exam reservation information, the image processing information, the situation information, and the transfer destination of the processing result image will be described later with reference to FIGS. 10 to 15.

Figure 8A:
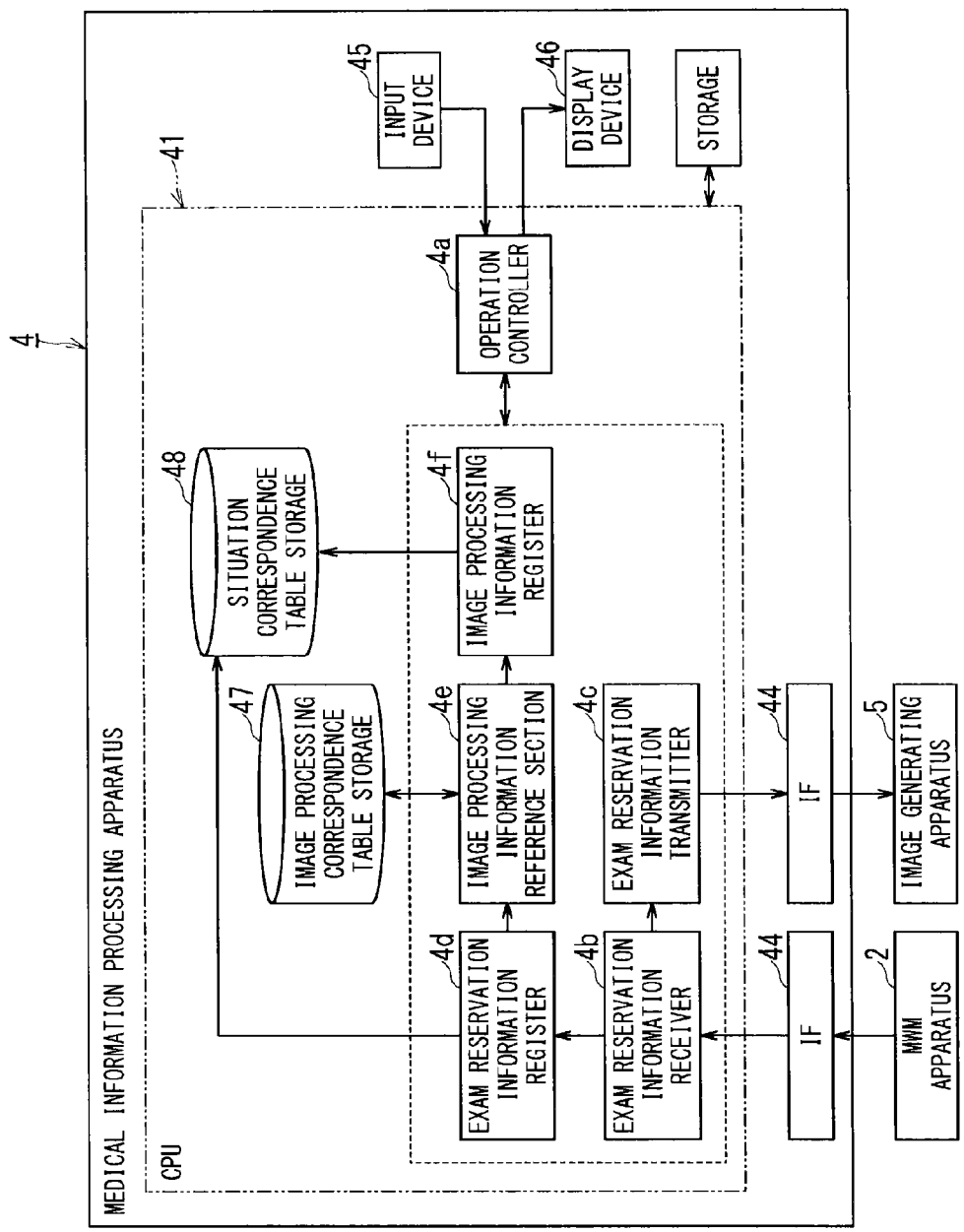
FIGS. 8A and 8B are block diagrams showing functions of the medical information processing apparatus according to the present embodiment.
Figure 8B:
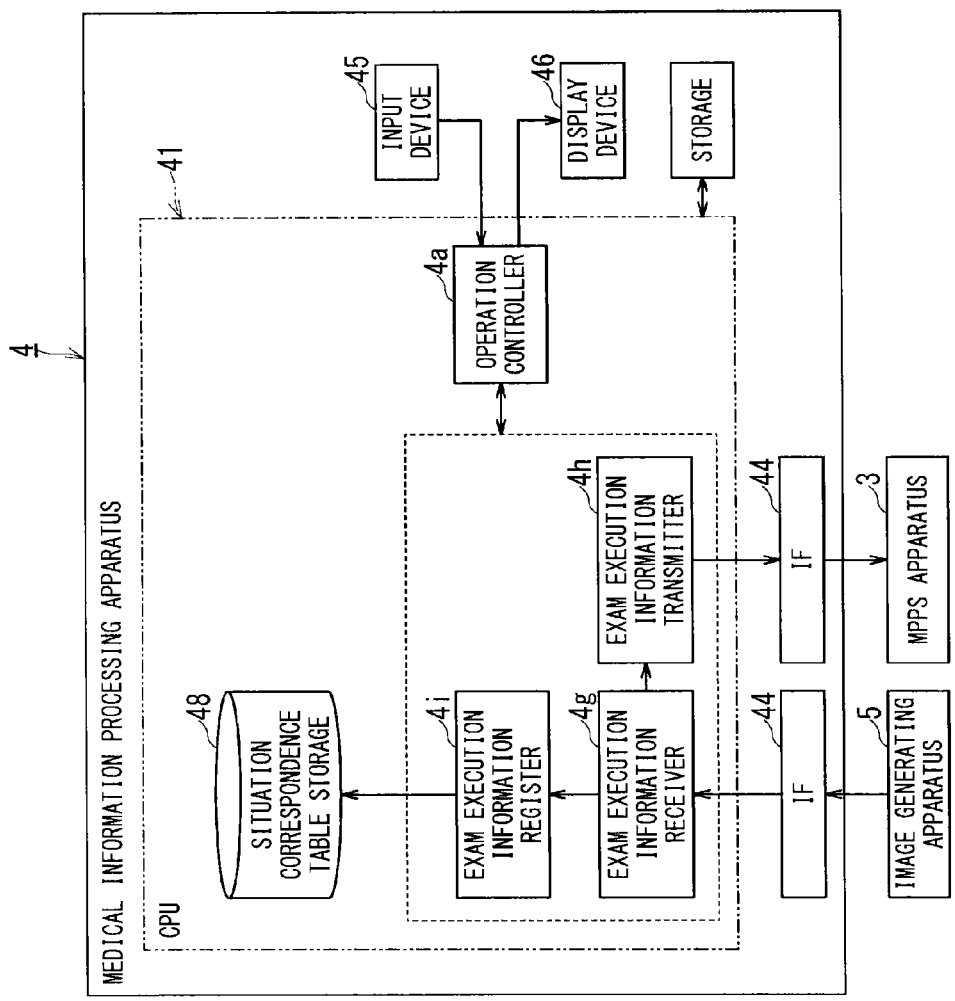
Figure 9:
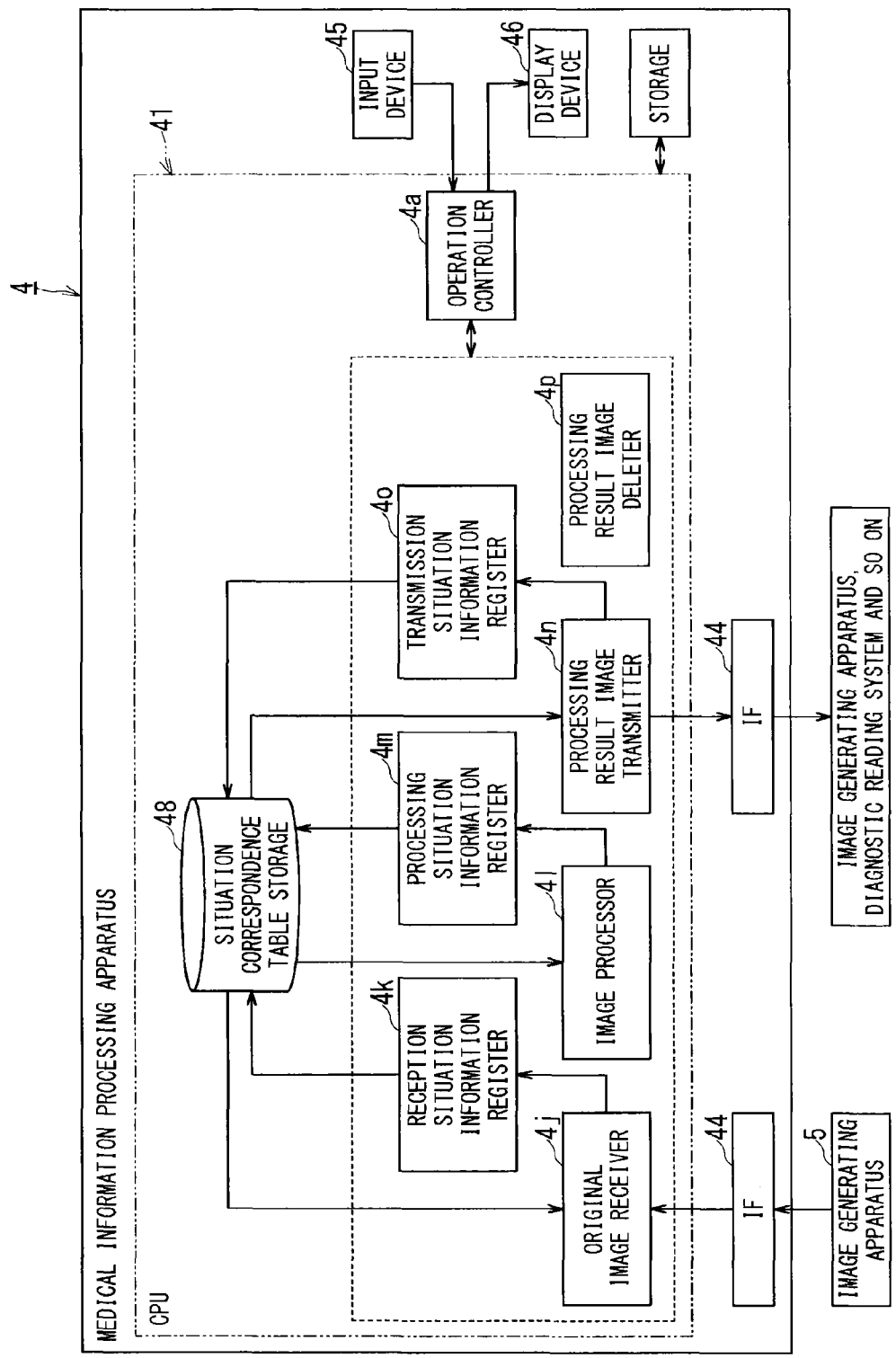
FIG. 9 is a block diagram showing functions of the medical information processing apparatus according to the present embodiment.

FIGS. 8A, 8B and 9 are block diagrams showing functions of the medical information processing apparatus 4 according to the present embodiment.

As shown in FIGS. 8A, 8B and 9, through execution of programs by the CPU 41, the medical information processing apparatus 4 functions as an operation controller 4a, an exam reservation information receiver 4b, an exam reservation information transmitter 4c, an exam reservation information register 4d, an image processing information reference section 4e, an image processing information register 4f, an exam execution information receiver 4g, an exam execution information transmitter 4h, an exam execution information register 4i, an original image receiver 4j, a reception situation information register 4k, an image processor 4l, a processing situation information register 4m, a processing result image transmitter 4n, a transmission situation information register 4o, and a processing result image deleter 4p. The description is made using the case where the configuration elements 4a to 4p function by means of software. Alternatively, some or all of the configuration elements 4a to 4p may be provided as hardware in the medical information processing apparatus 4.

The operation controller 4a shown in FIGS. 8A, 8B and 9 is an interface, such as a GUI (graphical user interface), mediating between the configuration elements 4b to 4p and the input device 45 and the display device 46.

Referring to FIG. 8A, the exam reservation information receiver 4b has a function of receiving the exam reservation information (shown in FIG. 3) as DICOM_MWM from the MWM apparatus 2 via the IF 44.

The exam reservation information transmitter 4c has a function of transmitting the exam reservation information received by the exam reservation information receiver 4b, to the image generating apparatus 5 via the IF 44.

The exam reservation information register 4d has a function of registering the exam detailed information of the exam reservation information received by the exam reservation information receiver 4b, into the situation correspondence table in the situation correspondence table storage 48.

Referring to FIGS. 10 to 15, the operation of the medical information processing apparatus 4 is described.

FIG. 10 is a diagram showing an example of the situation correspondence table at a first point in time.

FIG. 10 shows the situation correspondence table at the first point in time. At the first point in time, "not executed" is registered in the execution situation information in the situation correspondence table, and "not received" is registered in the reception situation information. FIG. 10 is the exam detailed information of the exam reservation information on two patients (patients A and B shown in FIG. 3).

Referring back to FIG. 8A, the image processing information reference section 4e has a function of referring to the image processing correspondence table (shown in FIG. 7) stored in the image processing correspondence table storage 47 for the exam detailed information contained in the exam reservation information (shown in FIG. 3) registered by the exam reservation information register 4d, and determining the image processing information corresponding to the exam detailed information.

The image processing information register 4f has a function of registering the image processing information corresponding to the exam detailed information determined by the image processing information reference section 4e, into the situation correspondence table in the situation correspondence table storage 48.

FIG. 11 is a diagram showing an example of the situation correspondence table at a second point in time.

FIG. 11 shows the situation correspondence table on the second point in time subsequent to the first point in time. The image processing information acquired from the image processing correspondence table (shown in FIG. 7) is registered in the situation correspondence table. "Not processed" is registered in the processing situation information for each type of image processing in the situation correspondence table, and "not transmitted" is registered in the transmission situation information for each transfer destination of the processing result image.

Referring to FIG. 8B, the exam execution information receiver 4g has a function of receiving each series of pieces of exam execution information (shown in FIG. 5) as DICOM_MPPS, from the image generating apparatus 5 via the IF 44.

The exam execution information transmitter 4h has a function of transmitting each series of pieces of exam execution information received by the exam execution information receiver 4g, to the MPPS apparatus 3 via the IF 44.

The exam execution information register 4i has a function of registering (updating) each series of pieces of exam execution information received by the exam execution information transmitter 4h, in the situation correspondence table in the situation correspondence table storage 48.

FIG. 12 is a diagram showing an example of the situation correspondence table at a third point in time.

FIG. 12 shows the situation correspondence table at a third point in time subsequent to the second point in time. According to the execution situation information representing completion of execution contained in the received exam execution information, the execution situation information in the situation correspondence table is updated from "not executed" to "completed". According to the execution situation information that is contained in the received exam execution information and represents that the exam is in progress, the execution situation information in the situation correspondence table is updated from "not executed" to "in progress". An exam with the execution situation information in the situation correspondence table that represents "not executed" is preferentially executed (in progress), and subsequently execution is completed (completed).

At the third point in time, the X-ray CT apparatus as an image generating apparatus 5 (shown in FIG. 8B) has completed execution of a series 1 of the exam A (collection of CT images as original images), the X-ray CT apparatus has completed execution of a series 2 of the exam A (collection of CT images), and the PET apparatus is executing a series 3 of the exam A (collection of PET images as original images). Furthermore, at the third point in time, the X-ray CT apparatus as the image generating apparatus 5 (shown in FIG. 8B) is executing a series 1 of a exam B (collection of CT images), the X-ray CT apparatus does not execute a series 2 of the exam B (collection of CT images) yet, and the MR apparatus does not execute a series 3 of the exam B (collection of MR images as original images) yet.

Here, according to the foregoing description with reference to FIGS. 1 to 8B, the exam reservation information (shown in FIG. 3) is transmitted from the MWM apparatus 2 through the medical information processing apparatus 4 to the image generating apparatus 5. However, the implementation is not limited to this case. The exam reservation information (shown in FIG. 3) may be transmitted from the MWM apparatus 2 to the medical information processing apparatus 4 and the image generating apparatus 5 in parallel. In this case, it is appropriate that the MWM apparatus 2 register a new medical information processing apparatus 4 in addition to the conventional image generating apparatus 5 as the destination of the exam reservation information (shown in FIG. 3). In this case, the registration negates the need of the exam reservation information transmitter 4c (shown in FIG. 8A).

Furthermore, according to the foregoing description with reference to FIGS. 1 to 8B, the exam execution information (shown in FIG. 5) is transmitted from the image generating apparatus 5 through the medical information processing apparatus 4 to the MPPS apparatus 3. However, the implementation is not limited to this case. The exam execution information (shown in FIG. 5) may be transmitted from the image generating apparatus 5 to the MPPS apparatus 3 and the medical information processing apparatus 4 in parallel. In this case, it is appropriate that the image generating apparatus 5 register a new medical information processing apparatus 4 in addition to the conventional MPPS apparatus 3, as the destination of exam execution information (shown in FIG. 5). In this case, the registration negates the need of the exam execution information transmitter 4h (shown in FIG. 8B).

Referring to FIG. 9, the original image receiver 4j has a function of referring to the situation correspondence table in the situation correspondence table storage 48, determining whether image processing is required or not (whether the image processing information is set or not), and, if determining that the image processing is required, referring to the situation correspondence table, actively issuing a transmission request for a group of original images (group of raw images) in units of series corresponding to images whose execution situation information is "completed" and whose reception situation information is "not received", and receiving the original images from the image generating apparatus 5 via the IF 44. Referring to the situation correspondence table (shown in FIG. 12) at the third point in time, the original image receiver 4j issues a transmission request for the group of original images pertaining to the series 1 and 2 of the exam A. Referring to the situation correspondence table (shown in FIG. 12) at the third point in time, the original image receiver 4j is in a state where completion of exams pertaining to the series 1 of the exam A and the series 1 to 3 of the exam B is waited.

Furthermore, the original image receiver 4j has a function of storing the received group of original images in units of series in a storage, such as the HDD 43.

The reception situation information register 4k has a function of registering (updating) the reception situation information that represents a reception situation of the group of original images in units of series in the original image receiver 4j into the situation correspondence table in the situation correspondence table storage 48.

FIG. 13 is a diagram showing an example of the situation correspondence table at a fourth point in time.

FIG. 13 shows the situation correspondence table at the fourth point in time subsequent to the third point in time. According to the reception situation of the group of original images in a unit of series, the reception situation information in the situation correspondence table is updated from "not received" to "completed" or from "not received" to "in reception". The group of original images whose execution situation information in the situation correspondence table is "completed" and whose reception situation information in this table is "not received" is preferentially received (in reception), and subsequently the reception is completed (completed).

At the fourth point in time, the group of CT images of the series 1 of the exam A whose execution situation information is "completed" is received, the group of CT images of the series 2 of the exam A whose execution situation information is "completed" is being received, and the group of PET images of the series 3 of the exam A whose execution situation information is "completed" is being received. At the fourth point in time, the group of CT images of the series 1 of the exam B whose execution situation information is "completed" is not received yet, the group of CT images of the series 2 of the exam B whose execution situation information is "in progress" is not received yet, and the group of MR images of the series 3 of the exam B whose execution situation information is "not executed" is not received yet.

Referring back to FIG. 9, the image processor 4l has a function of referring to the situation correspondence table in the situation correspondence table storage 48, acquiring the group of original images in units of types of image processing corresponding to images whose reception situation information is "completed" and whose processing situation information is "not processed" from the storage, and performing image processing to generate a processing result image as a DICOM image. Referring to the situation correspondence table at the fourth point in time (shown in FIG. 13), the image processor 4l applies image processing to the group of original images of the series 1 of the exam A. Thus, referring to the situation correspondence table at the fourth point in time (shown in FIG. 13), the image processor 4l is in a state of waiting completion of reception of the group of original images pertaining to the series 2 and 3 of the exam A and the series 1 to 3 of the exam B.

Furthermore, in the case whose image processing information contains information through a 3D fusion process, after reception of all the group of original images required for the 3D fusion process, the image processor 4*l* performs the 3D fusion process using the group of original images, and generates a 3D fused image (a resultant image of the 3D fusion process) as a processing result image. Referring to the situation correspondence table at the fourth point in time (shown in FIG. 13), the image processor 4*l* performs the 3D fusion process using not only the group of original images on the series 1 of the exam A having already been received but also the group of original images pertaining to the series 1 and 3, when the group of original images pertaining to the series 3 of the exam A is received.

The image processor 4*l* further has a function of storing the processing result image as a DICOM image in a storage, such as the HDD 43. A configuration may be adopted that causes the image processing apparatus 6 (shown in FIG. 1) to execute the image processing.

The processing situation information register 4*m* has a function of registering (updating) the processing situation information that represents a situation of image processing by the image processor 4*l* into the situation correspondence table of the situation correspondence table storage 48.

FIG. 14 is a diagram showing an example of the situation correspondence table at a fifth point in time.

FIG. 14 shows the situation correspondence table at the fifth point in time subsequent to the fourth point in time. According to the situation of image processing by the group of original images in units of types of image processing, the processing situation information in the situation correspondence table is updated from "not processed" to "completed" or from "not processed" to "in process". The group of original images whose reception situation information in the situation correspondence table is "completed" and whose processing situation information in this table is "not processed" are preferentially image-processed (in process), and subsequently the image processing is completed (completed).

At the fifth point in time, the myocardium extracting process based on the group of CT images which are the original images of the series 1 of the exam A and whose reception situation information is "completed" is completed, the coronary artery extracting process based on the group of CT images of the series 2 of the exam A whose reception situation information is "completed" is completed, the process of generating cardiac metabolism images for a processing result image based on the group of PET images which are the original images of the series 3 of the exam A and whose reception situation information is "completed" is completed, and the 3D fusion process based on the group of CT images of the series 1 of the exam A and the group of PET images of the series 3 of the exam A is completed. At the fifth point in time, a cerebrovascular vessel extracting process based on the group of CT images of the series 2 of the exam B whose reception situation information is "completed" is being performed, a tractography image generating process based on the group of MR images as the original images of the series 3 of the exam B whose reception situation information is "not received" is not processed yet, and the 3D fusion process based on the group of CT images of the series 1 of the exam B whose reception situation information is "completed" and the group of MR images of the series 3 of the exam B whose reception situation information is "not received" is not performed yet.

Referring back to FIG. 9, the processing situation information register 4*m* may register information, such as the type of the image generating apparatus 5, the type of image processing, and the processing situation information on the image processing, as comments into the exam reservation information as DICOM_MWM. In this case, through looking up the exam reservation information, the operator can view states of images pertaining to a certain patient, i.e., a generated state (processing situation information: "completed") and a state of being scheduled to be generated (processing situation information: "not executed" or "in progress"). Furthermore, the operator can look up the exam reservation information to select a desired a processing result image whose processing situation information is "completed".

The processing result image transmitter 4*n* has a function of referring to the situation correspondence table in the situation correspondence table storage 48, and acquiring a processing result image whose processing situation information is "completed" and whose transmission situation information is "not transmitted" from the storage. The processing result image transmitter 4*n* further has a function of transmitting the acquired processing result image to the transfer destination of a processing result image via the IF 44 in conformity with the DICOM standard. Referring to the situation correspondence table at the fifth point in time (shown in FIG. 14), the processing result image transmitter 4*n* transmits a myocardium image (a resultant image of a myocardium extracting process), a coronary artery image (a resultant image of a coronary artery extracting process), a cardiac metabolism image and a 3D fused image, which are processing result images, to the X-ray CT apparatus 5 and the diagnostic reading system 9. Referring to the situation correspondence table at the fifth point in time (shown in FIG. 14), the processing result image transmitter 4*n* is in a state where completion of the cerebrovascular vessel extracting process, the tractography image generation, and 3D fusion is waited.

The transmission situation information register 4*o* has a function of registering (updating) the transmission situation information that represents the situation of transmission of the processing result image in the processing result image transmitter 4*n* into the situation correspondence table of the situation correspondence table storage 48.

FIG. 15 is a diagram showing an example of the situation correspondence table at a sixth point in time.

FIG. 15 shows the situation correspondence table at the sixth point in time subsequent to the fifth point in time. According to the situation of transmission of the processing result image, the transmission situation information in the situation correspondence table is updated from "not transmitted" to "completed" or from "not transmitted" to "in transmission". A processing result image whose processing situation information in the situation correspondence table is "completed" and whose transmission situation information in this table is "not transmitted" is preferentially transmitted (in transmission), and subsequently the transmission is completed (completed).

At the sixth point in time, transmission of the myocardium image, the coronary artery image, the cardiac metabolism image and the 3D fused image which are processing result images and whose processing situation information is "completed" to the X-ray CT apparatus 5 is completed, and the myocardium image, the coronary artery image, the cardiac metabolism image and the 3D fused image whose processing situation information is "completed" are being transmitted to the diagnostic reading system 9. At the sixth point in time, the cerebrovascular image (the resultant image of the cerebrovascular vessel extracting process), the tractography image, and the 3D fused image are not transmitted to the MR apparatus 5 and the diagnostic reading system 9 yet.

Referring back to FIG. 9, the processing result image deleter 4p has a function of deleting the processing result image from the storage at a required time after the start of storing the image into the storage. Alternatively, the processing result image deleter 4p may delete, from the storage, the processing result image having been transmitted to the transfer destination of a processing result image.

The medical information processing apparatus 4 according to the present embodiment can determine the type of image processing on the basis of the exam reservation information specified in the DICOM standard, apply the determined type of image processing to the original images to generate the processing result image, thereby allowing the efficiency of the image processing to be improved.

Furthermore, the medical information processing apparatus 4 according to the present embodiment can automatically determine whether the image processing is required or not using the exam reservation information and the exam execution information specified in the DICOM standard as reference information. If it is determined that the image processing is required, reception of the group of original images required for the image processing, the image processing through use of the group of original images, and transmission of the processing result image are actively performed. This performance can reduce the waiting time required for transfer of the processing result image and image processing while omitting time and effort to be performed through manual procedures therefore. Accordingly, the efficiency of diagnosis (diagnostic reading)/treatment through use of the processing result image can be improved.

(First Modification)

The image generating apparatus 5 (shown in FIGS. 8A and 8B) may include different multiple modalities, such as a PET-CT apparatus and a PET-MR apparatus. The case of adopting a PET-CT apparatus as an image generating apparatus 5 is described using the situation correspondence table at the third point in time shown in FIG. 12. The PET-CT apparatus as the image generating apparatus 5 has completed the execution of the series 1 of the exam A (collection of CT images as original images), the PET-CT apparatus has completed the execution of the series 2 of the exam A (collection of CT images), and the PET-CT apparatus is executing the series 3 of the exam A (collecting PET images as original images).

(Second Modification)

The case of preliminarily setting the image processing information in the image processing correspondence table shown in FIG. 7 has been described. Alternatively, the image processing information may be acquired from the exam reservation information shown in FIG. 3. In this case, individual pieces of exam reservation information received by the respective individual image generating apparatuses are assigned image processing information (including information through a 3D fusion process).

If the image processing information is included in the exam reservation information, the medical information processing apparatus 4 performs image processing according to the image processing information. On the contrary, if the image processing information is not included in the exam reservation information, the image processing is performed according to the image processing information in the image processing correspondence table shown in FIG. 7. Thus, even in the case where special image processing different from a normal routine is required (the case where the image processing information is included in the exam reservation information), individual processing can be performed without changing the entire rule set in the medical information processing apparatus 4. Accordingly, the time and effort of the operator can be reduced, and an efficient environment can be provided.

(Third Modification)

The image processing information reference section 4e shown in FIG. 8A may refer to the image processing correspondence table (shown in FIG. 7) stored in the image processing correspondence table storage 47 for the exam detailed information included in the exam execution information (shown in FIG. 5) received by the exam execution information receiver 4g, and determine the image processing information corresponding to the exam detailed information. In this case, the medical information processing apparatus 4 does not necessarily include the exam reservation information receiver 4b, the exam reservation information transmitter 4c, and the exam reservation information register 4d. If the medical information processing apparatus 4 does not include these elements, the MWM apparatus 2 directly transmits the exam reservation information as DICOM_MWM to the image generating apparatus 5.

If the image processing information reference section 4e determines the image processing information corresponding to the exam execution information, the image processing correspondence table storage 47 stores the image processing correspondence table that represents correspondence relationship between the exam detailed information included in the exam execution information (shown in FIG. 5) and the image processing information (type of image processing). The image processing correspondence table storage 47 preliminarily includes the image processing information for acquiring a processing result image having a high possibility of being used by the operator (diagnostic reader).

Here, in the case where the image processing information reference section 4e determines the image processing information corresponding to the exam reservation information, the exam detailed information shown in FIGS. 10 to 15 is based on the exam reservation information. The exam identifying information and the execution situation information included in the exam execution information are added to the exam detailed information included in the exam reservation information in the situation correspondence table shown in FIG. 11, and the situation correspondence tables (shown in FIGS. 12 to 15) are sequentially generated.

Alternatively, in the case where the image processing information reference section 4e determines the image processing information corresponding to the exam execution information, the exam detailed information shown in FIGS. 10 to 15 is based on the exam execution information. After execution of the exam, the situation correspondence table that includes the exam detailed information, the exam identifying information and the execution situation information that are contained in the exam execution information is generated. That is, in the case where the image processing information reference section 4e determines the image processing information corresponding to the exam execution information, the exam reservation information is not required.

Referring to FIGS. 16 to 19, the operation of a third example of the medical information processing apparatus 4 is described.

FIG. 16 is a diagram showing an example of a situation correspondence table at a first point in time.

FIG. 16 shows the situation correspondence table at the first point in time. According to the reception situation of the group of original images in units of series, "completed" is registered as the execution situation information in the situation correspondence table (reception situation information).

At the first point in time shown in FIG. 16, the execution (reception) of the group of CT images of the series 1 of the exam A whose execution situation information is "completed" is completed.

FIG. 17 is a diagram showing an example of the situation correspondence table at a second point in time.

FIG. 17 shows the situation correspondence table at the second point in time subsequent to the first point in time shown in FIG. 16. According to the reception situation of the group of original images in units of series, "completed" is registered as the execution situation information (reception situation information) in the situation correspondence table.

At the second point in time shown in FIG. 17, the execution (reception) of the group of CT images (normal imaging) of the series 1 of the exam A whose execution situation information is "completed" is completed, the execution of the group of CT images (contrast imaging) of the series 2 of the exam A whose execution situation information is "completed" is completed, and the execution of the group of PET images of the series 3 of the exam A whose execution situation information is "completed" is completed. At a fifth point in time, execution of the group of CT images (normal imaging), the group of CT images (contrast imaging) and the group of PET images is completed. Therefore, at the fifth point in time, from the image processing correspondence table (shown in FIG. 7), the image processing information according to the combination of the groups of images is determined.

At the second point in time shown in FIG. 17, "not processed" is registered in the processing situation information for each image processing in the situation correspondence table, and "not transmitted" is registered in the transmission situation information for each transfer destination of a processing result image.

FIG. 18 is a diagram showing an example of the situation correspondence table at a third point in time.

FIG. 18 shows the situation correspondence table at the third point in time subsequent to the second point in time shown in FIG. 17. According to the situation of image processing for the group of original images in units of types of image processing, the processing situation information in the situation correspondence table is updated from "not processed" to "completed". The group of original images whose reception situation information in the situation correspondence table is "completed" and whose processing situation information in this table is "not processed" are preferentially image-processed (in process), and subsequently the image processing is completed (completed).

At the third point in time shown in FIG. 18, a myocardium extracting process based on the group of CT images as the original images of the series 1 of the exam A whose reception situation information is "completed" is completed, a coronary artery extracting process based on the group of CT images of the series 2 of the exam A whose reception situation information is "completed" is completed, a process of generating cardiac metabolism images as a processing result image based on the group of PET images as the original images of the series 3 of the exam A whose reception situation information is "completed" is completed, and a 3D fusion process based on the group of CT images of the series 1 of the exam A and the group of PET images of the series 3 of the exam A is completed.

FIG. 19 is a diagram showing an example of the situation correspondence table at the fourth point in time.

FIG. 19 shows the situation correspondence table at the fourth point in time subsequent to the third point in time shown in FIG. 18. According to the transmission situation of the processing result image, the transmission situation information in the situation correspondence table is updated from "not transmitted" to "completed" or from "not transmitted" to "in transmission". A processing result image whose processing situation information in the situation correspondence table is "completed" and whose transmission situation information in this table is "not transmitted" is preferentially transmitted (in transmission), and subsequently the transmission is completed (completed).

At the fourth point in time shown in FIG. 19, transmission of the myocardium image, the coronary artery image, the cardiac metabolism image and the 3D fused image whose processing situation information is "completed" as processing result images to the X-ray CT apparatus 5 is completed, and the myocardium image, the coronary artery image, the cardiac metabolism image and the 3D fused image whose processing situation information is "completed" is being transmitted to the diagnostic reading system 9. Furthermore, at the fourth point in time, the cerebrovascular image (the resultant image of the cerebrovascular vessel extracting process), the tractography image and the 3D fused image are not transmitted yet to the MR apparatus 5 and the diagnostic reading system 9 yet.

The third example of the medical information processing apparatus 4 according to the present embodiment can determine the type of image processing on the basis of the exam execution information specified in the DICOM standard, apply the determined type of image processing to the original images to generate the processing result image, thereby allowing the efficiency of the image processing to be improved.

Furthermore, the third example of the medical information processing apparatus 4 according to the present embodiment can automatically determine whether the image processing is required or not using the exam execution information specified in the DICOM standard as reference information. If it is determined that the image processing is required, reception of the group of original images required for image processing, image processing through use of the group of original images, and transmission of the processing result image are actively performed. This performance can reduce the waiting time required for transfer of the processing result image and image processing while omitting time and effort to be performed through manual procedures. Accordingly, the efficiency of diagnosis (diagnostic reading)/treatment through use of the processing result image can be improved.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical information processing apparatus connected to image generating apparatuses and an exam reservation apparatus via an intercommunication network, comprising:
processing circuitry configured to
receive exam reservation information for the image generating apparatuses, from the exam reservation apparatus,
determine a type of image processing based on the received exam reservation information,
apply the determined type of image processing to original medical images generated by and received from the image generating apparatuses via the intercommunication network, to generate a processing result image, and
receive exam execution information from the image generating apparatuses via the intercommunication network, the exam execution information representing an exam execution situation and corresponding to the received exam reservation information, wherein
the processing circuitry is further configured to apply the determined type of image processing to the original medical images based on the exam execution information corresponding to the exam reservation information.

2. The medical information processing apparatus according to claim 1, further comprising:
a memory to store the original medical images and the processing result image.

3. The medical information processing apparatus according to claim 2, wherein the processing circuitry is further configured to delete the processing result image from the memory after a required time has elapsed.

4. The medical information processing apparatus according to claim 1, wherein the processing circuitry is further configured to
determine whether the image processing is required or not according to the received exam reservation information, and
issue a request for transmitting the original medical images generated through completion of execution of the exam and receive the original medical images, when the determiner determines that the image processing is required to be applied to the original medical images generated by the image generating apparatuses based on the exam reservation information, and determines that execution of the exam is completed based on the exam execution information corresponding to the received exam reservation information.

5. The medical information processing apparatus according to claim 4, wherein the processing circuitry is further configured to perform, when a 3D fusion process is included in the determined type of image processing, the 3D fusion process upon receipt of all the original medical images corresponding to a type of the image generating apparatus, which is included in the exam reservation information.

6. The medical information processing apparatus according to claim 4, wherein the processing circuitry is further configured to transmit the processing result image to an external transfer destination set according to the received exam reservation information.

7. The medical information processing apparatus according to claim 1, wherein the processing circuitry is further configured to determine the type of image processing, based on an image processing correspondence table associating the exam reservation information and the type of image processing with each other.

8. The medical information processing apparatus according to claim 7, wherein the correspondence table preliminarily includes the type of image processing for acquiring the processing result image having a high possibility of being used by an operator.

9. The medical information processing apparatus according to claim 1, wherein the processing circuitry is further configured to determine the type of image processing for the original medical images, based on an image processing correspondence table associating a combination and the type of image processing with each other, the combination being between the exam reservation information and the image generating apparatuses.

10. The medical information processing apparatus according to claim 1, wherein the processing circuitry is further configured to determine the type of image processing based on the exam reservation information, which includes at least one of a type of each image generating apparatus, an imaging condition used by each image generating apparatus, and a target site.

11. The medical information processing apparatus according to claim 1, wherein the processing circuitry is further configured to receive the exam reservation information, which includes exam detailed information and patient identifying information, the exam detailed information representing a content of an exam.

12. The medical information processing apparatus according to claim 11, wherein the processing circuitry is further configured to determine the type of image processing for the original medical images based on the exam detailed information.

13. A medical information processing apparatus connected to image generating apparatuses and an exam reservation apparatus via an intercommunication network, comprising:
processing circuitry configured to
receive exam reservation information for the image generating apparatuses, from the exam reservation apparatus,
determine a type of image processing based on the received exam reservation information, and
apply the determined type of image processing to original medical images generated by and received from the image generating apparatuses via the intercommunication network, to generate a processing result image, wherein
the processing circuitry is further configured to determine the type of image processing, based on an image processing correspondence table associating the exam reservation information and the type of image processing with each other, the correspondence table preliminarily including the type of image processing for acquiring the processing result image having a high possibility of being used by an operator.

14. A medical information processing apparatus connected to image generating apparatuses and an exam reservation apparatus via an intercommunication network, comprising:
processing circuitry configured to
receive exam reservation information for the image generating apparatuses, from the exam reservation apparatus,
determine a type of image processing based on the received exam reservation information, and apply the determined type of image processing to original medical images generated by and received from the image generating apparatuses via the intercommunication network, to generate a processing result image, wherein
the processing circuitry is further configured to determine the type of image processing for the original medical images, based on an image processing correspondence table associating a combination and the type of image processing with each other, the combination being between the exam reservation information and the image generating apparatuses.

* * * * *